United States Patent
Furuya et al.

(10) Patent No.: US 6,392,090 B1
(45) Date of Patent: *May 21, 2002

(54) PROCESS FOR PREPARING HYDROXYBENZOIC ACIDS

(75) Inventors: Masayuki Furuya; Akinori Nagatomo; Masaru Wada, all of Fukuoka (JP)

(73) Assignee: Mitsui Chemicals, Inc. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/938,833

(22) Filed: Sep. 26, 1997

(30) Foreign Application Priority Data

Oct. 2, 1996 (JP) .............................................. 8-261715
Dec. 16, 1996 (JP) .............................................. 8-335516

(51) Int. Cl.$^7$ .............................................. C07C 51/15
(52) U.S. Cl. ....................................... 562/424; 562/405
(58) Field of Search ................................ 562/424, 405

(56) References Cited

U.S. PATENT DOCUMENTS 4,032,555 A    6/1977    Bottaccioi et al. .......... 558/406

FOREIGN PATENT DOCUMENTS

| GB | 734605 | 9/1955 |
| GB | 1561334 | 2/1980 |
| JP | 63-165341 | 7/1988 |
| JP | 64-34944 | 2/1989 |
| JP | 3-90047 | 4/1991 |
| JP | 3-178947 | 8/1991 |

*Primary Examiner*—Paul J. Killos
*Assistant Examiner*—Taylor V. Oh
(74) *Attorney, Agent, or Firm*—Burns, Doane, Swecker & Mathis, LLP

(57) ABSTRACT

A process for preparing a hydroxybenzoic acid is herein disclosed which comprises reacting a phenol with an alkali metal compound by the use of an aprotic polar organic solvent as a reaction solvent to form an alkali metal salt of the phenol, and then reacting this alkali metal salt with carbon dioxide to obtain a hydroxybenzoic acid, said process comprising the step of carrying out the reaction under conditions that a molar ratio of the phenol to the total of the alkali metal compound and the aprotic polar organic solvent is larger than 1. Furthermore, the process may contain the steps of precipitating crystals from the reaction solution, separating the solid from the solution to obtain a wet alkali metal salt of the hydroxybenzoic acid, dissolving the wet alkali metal salt in water, and precipitating crystals from the solution by acidification to obtain the hydroxybenzoic acid.

7 Claims, No Drawings

PROCESS FOR PREPARING HYDROXYBENZOIC ACIDS

BACKGROUND OF THE INVENTION (i) Field of the Invention

The present invention relates to a process for preparing hydroxybenzoic acids. More specifically, it relates to an industrially advantageous process for preparing alkylsalicylic acids such as a 3,5-dialkylsalicylic acid which are useful as synthetic materials of chemicals such as developers for pressure-sensitive recording papers, agricultural chemicals and antioxidants.

(ii) Description of the Prior Art

As a process for preparing a hydroxybenzoic acid, there is known the Kolbe-Schmidt reaction from old days which comprises reacting an alkali metal salt of a phenol with carbon dioxide.

In recent years, as improved techniques of the Kolbe-Schmidt reaction, methods in which the reaction proceeds in the state of a solution or a slurry instead of a solid phase reaction have intensively been researched from the viewpoint of some industrial advantages.

For example, Japanese Patent Application Laid-open No. 165341/1988 discloses a method for preparing a 3,5-dialkylsalicylic acid which comprises adding an aqueous alkali metal hydroxide solution and a 2,4-dialkylphenol to a hydrocarbon solvent, the amount of the 2,4-dialkylphenol being in excess of the alkali, removing water by azeotropic dehydration to synthesize an anhydrous alkali metal salt of the 2,4-dialkylphenol, and reacting this salt with carbon dioxide. In this method, however, the reaction mass tends to form a paste, which makes stirring difficult. In consequence, as shown in comparative examples which will be described hereinafter, a sufficient reaction yield cannot be obtained.

Japanese Patent Application Laid-open No. 34944/1989 discloses a reaction in a mixed solvent of a hydrocarbon solvent such as toluene and sulfolane, but sulfolane is a viscous and high-boiling solvent; and hence, because of the adhesion of sulfolane to crystals, it is difficult to recover all of the sulfolane.

In a method disclosed in Japanese Patent, Application Laid-open No. 178947/1991, a 2,4-dialkylphenol is reacted with an alkali metal hydroxide in a lower alcohol, and the lower alcohol and produced water are then distilled off. The resulting anhydrous alkali metal salt of the 2,4-dialkylphenol is next reacted with carbon dioxide. However, the reaction with carbon dioxide is carried out in a non-solvent solid phase state, which is not considered to be an industrially advantageous method.

In Japanese Patent Application Laid-open No. 90047/1991, there is disclosed a method which comprises heating a 2,4-dialkylphenol and an alkali metal hydroxide in a mixed solvent of a hydrocarbon solvent and 1,3-dimethyl-2-imidizolidinone, carrying out azeotropic dehydration to form an anhydrous alkali metal salt of the 2,4-dialkylphenol, reacting the same with carbon dioxide in the mixed solvent to obtain a 3,5-dialkylsalicylic acid. In this method, the reaction solution is directly discharged into an acidic liquid to take out the product. However, it is difficult to recover expensive 1,3-dimethyl-2-imidazolidinone from the aqueous layer, and so this method is not considered to be an industrially advantageous method. In addition, it is described in the disclosed specification that the amount of 1,3-dimethyl-2-imidazolidinone to be used is preferably in the range of 1 to 5 wt % based on the weight of the raw material phenol from an economical viewpoint, but when the compound is used in such an amount, the reaction system becomes a paste at the time of the dehydration, so that the reaction system is substantially close to the state of a solid reaction and hence stirring by a conventional of stirrer is impossible. Even if the reaction is forcedly continued, a sufficient reaction yield cannot be obtained.

In the case that the reaction is carried out in an aprotic polar organic solvent such as sulfolane or 1,3-dimethyl-2-imidazolidinone, the high reaction yield can be obtained, but as described above, there are large problems regarding the recovery of the product from the reaction solution and the recovery of the solvent.

That is to say, in the case that the aprotic copolar organic solvent is used as the reaction solvent, the reaction proceeds to a the high reaction yield, but o after the reaction, even if it is attempted that the alkali metal salt of the 3,5-dialkylsalicylic acid is crystallized and collected from the reaction solution, the recovery yield is much lower as compared with the reaction yield, because the solubility of this metal salt in the aprotic polar organic solvent is high. It is also possible that a large amount of a poor solvent can be added to recover the product, but the volume efficiency is very poor. Furthermore, a wet type of the obtained alkali metal salt of the 3,5-dialkylsalicylic acid contains a large amount of the aprotic polar organic solvent. Since a certain interaction is present between the alkali metal salt of the 3,5-dialkylsalicylic acid and the aprotic polar organic solvent, the removal of the aprotic polar solvent by washing with the poor solvent is difficult. If the thus obtained alkali metal salt of the 3,5-dialkylsalicylic acid containing the aprotic polar organic solvent is dissolved in water to do acidifying-out, all of the contained aprotic organic solvent transfers to the crystallization by acidification filtrate and it is consequently lost.

As a technique other than the above crystallization for recovering the alkali metal salt of the 3,5-dialkylsalicylic acid, there is a method which comprises concentrating the reaction solution. In this method, however, the distillation efficiency of a high-boiling solvent such as 1,3-dimethyl-2-imidazolidinone or sulfolane is poor, and as described above, a certain interaction is present between the alkali metal salt of the 3,5-dialkylsalicylic acid and the aprotic polar organic solvent, so that the recovery of its total amount by the distillation is impossible.

On the other hand, even in the case that the reaction solution is directly dissolved in water with-out the alkali metal salt of the 3,5-dialkyl-salicylic acid and then separated, wherein the separated aqueous layer is further subjected to the acidifying-out, almost all aprotic polar organic solvent transfers to the acidifying-out filtrate and is finally lost. In order to recover the aprotic polar organic solvent in a large amount of water, it is necessary to distill a large amount of water, and for this reason, the technique is not industrially applicable in view of an energy efficiency. Thus, on the basis of the conception that the loss of the aprotic polar organic solvent is unavoidable, it can also be considered to reduce the amount of the aprotic polar organic solvent to be used from an economical viewpoint, but if the amount of the aprotic polar organic solvent is reduced, the reaction solution correspondingly becomes a substantially solid phase reaction in a paste state, so that the reaction yield also deteriorates.

SUMMARY OF THE INVENTION

In consequence, an object of the present invention is to provide an industrially applicable process for preparing a hydroxybenzoic acid from a phenol in accordance with the Kolbe-Schmidt reaction by the use of an aprotic polar organic solvent as a reaction solvent, and this process is excellent in reaction yield and product recovery yield and can substantially completely recover the used aprotic polar organic solvent.

The present inventors have intensively investigated with the intention of solving the problems of the conventional technique, and as a result, it has been found that in a process which comprises reacting a phenol with an alkali metal compound by the use of an aprotic polar organic solvent as a reaction solvent to form an alkali metal salt of the phenol, and then reacting this alkali metal salt with carbon dioxide to obtain a hydroxybenzoic acid, an alkali metal salt of the hydroxybenzoic acid can be quantitatively recovered by sufficiently raising the ratio of the phenol to the hydroxybenzoic acid and the aprotic polar organic solvent even after the reaction, and the obtained wet product does not contain any aprotic polar organic solvent. In consequence, the present invention has been completed.

That is to say, the present invention is directed to a process for preparing a hydroxybenzoic acid which comprises reacting a phenol with an alkali metal compound by the use of an aprotic polar organic solvent as a reaction solvent to form an alkali metal salt of the phenol, and then reacting this alkali metal salt with carbon dioxide to obtain the hydroxybenzoic acid, said process comprising the step of carrying out the reaction under conditions that a molar ratio of the phenol to the total of the alkali metal compound and the aprotic polar organic solvent is larger than 1; and further the steps of precipitating crystals from the reaction solution, separating the solid from the solution to obtain the wet alkali metal salt of the hydroxybenzoic acid, dissolving the wet alkali metal salt in water, and acidifying-out the solution to obtain the hydroxybenzoic acid.

DETAILED DESCRIPTION OF THE INVENTION

A In the present invention, an alkali metal compound and a phenol in an amount in excess of the alkali metal compound are heated in an aprotic polar organic solvent to form an alkali metal salt of the phenol. At this time, produced water is removed from the system, and after the completion of the dehydration, the obtained alkali metal salt of the phenol is then reacted with carbon dioxide to obtain a desired hydroxybenzoic acid.

No particular restriction is put on a kind of phenol which can be used in the present invention, and phenol and optionally substituted phenols can be used. Examples of the substituents include straight-chain and branched alkyl groups having 1 to 20 carbon atoms, alkenyl groups, alkoxy groups, acyl groups; a phenyl group, an amino group, a carboxyl group, a sulfonic group, thiol groups and a nitro group, and these groups may optionally be substituted. In addition, the number of the substituents is optional, and no particular restriction is put on a substituted position. In the case that the phenol has a plurality of substituents, these substituents may be the same or different.

Among these substituents, alkyl substituted phenols and alkoxy substituted phenols which possess a high reaction selectivity and a high reaction yield are preferable, and above all, dialkylphenols are preferable. Examples of the alkyl groups include methyl, ethyl, n-propyl, i-propyl, n-butyl, sec-butyl, tert-butyl, octyl and 2-ethylhexyl.

No particular restriction is put on the alkali metal compound which can be used in the present invention, and alkali metal hydroxides and alkali metal alcoholates can be used. From the viewpoints of the ease of handling and economy, however, alkali metal hydroxides typified by sodium hydroxide and potassium hydroxide can be used. They can be used in the state of a solid or an aqueous solution having an optional concentration.

The amount of the phenol for use in the present invention should be regulated so as to be 1 to 9 mols, preferably 2 to 6 mols per mol of the alkali metal salt of the produced hydroxybenzoic acid even after the completion of the reaction in addition to more than a mol equal to the aprotic polar organic solvent. If the ratio of the phenol to the alkali metal salt of the hydroxybenzoic acid is more than the above range, volume efficiency decreases. On the other hand, if the ratio of the phenol to the alkali metal salt of the hydroxybenzoic acid and the aprotic polar organic solvent is less than the above level, crystallization yield of the alkali metal salt of the hydroxybenzoic acid obtained by the reaction deteriorates, and in addition, the wet alkali metal salt of the hydroxybenzoic acid contains a large amount of the aprotic polar organic solvent. Therefore, when the wet product is dissolved in water and then separated, the total amount of the contained aprotic polar organic solvent transfers to the crystallization by acidification filtrate of the separated aqueous layer and it is finally lost. The above regulation of the amount of phenol may be carried out at the time of the feed of the phenol and the alkali metal compound for the reaction, before the reaction of the alkali metal salt of the phenol with carbon dioxide, during the reaction, or after the completion of the reaction. However, in the case that the regulation is done before the reaction of the alkali metal salt of the phenol with carbon dioxide, during the reaction, or after the completion of the reaction, it is necessary that the excess phenol should be removed from the recovered solution after the crystallization and the separation of the alkali metal salt of the hydroxybenzoic acid, and then be returned to a raw material system for the next reaction, which makes the efficiency low. Accordingly, it is most preferable that the regulation is carried out at the time of the feed of the phenol and the alkali metal compound for the reaction.

In the present invention, the phenol is preferably fed so as to be in the range of 2 to 10 mols per mol of the alkali metal compound and, in addition, so as to be 2 mols to 30 mols per mol of the aprotic polar organic solvent. As described above, if the amount of the phenol is more than this range, the volume efficiency decreases. On the other hand, if the ratio of the phenol is less than the above range, the crystallization yield of the alkali metal salt of the hydroxybenzoic acid obtained by the reaction deteriorates, and in addition, the wet alkali metal salt of the hydroxybenzoic acid contains a large amount of the aprotic polar organic solvent. Therefore, when the wet product is dissolved in water and then separated, the total. amount of the contained aprotic polar organic solvent transfers to the acidifying-out filtrate of the separated aqueous layer and it is finally lost.

Examples of the aprotic polar organic solvent which can be used in the present invention include amide solvents such as N,N-dimethylformamide, N,N-dimethylacetamide, N-methylpyrrolidone, 1,3-dimethyl-2-imidazolidinone, 1,3-dipropyl-2-imidazolidinone and 1,3-dibutyl-2-imidazolidinone, and sulfur-containing solvents such as dimethyl sulfoxide and sulfolane. These may be used singly or in a combination of two or more thereof. The organic solvent which is excellent in stability in the presence of the alkali metal compound is preferable, in particular, the employment of 1,3-dimethyl-2-imidazolidinone or sulfolane is preferable. The amount of the aprotic polar organic solvent to be used depends on the amount of the phenol to be used, but it is in the range of 0.3 to 3 mols, preferably 0.3 to 1.5 mols per mol of the alkali metal compound. If the amount of the aprotic polar organic solvent is less than the above range, the reaction system forms such a paste so that stirring is difficult by a conventional stirrer, and in addition, the sufficient reaction yield cannot be obtained. On the other hand, if the amount is more than the above range, the crystallization yield of the alkali metal salt of the hydroxybenzoic acid produced by the reaction deteriorates.

In the present invention, water produced during the formation of the alkali metal salt of the phenol from the phenol and the alkali metal compound is removed from the system under atmospheric pressure or reduced pressure, together with water which is accompanied by the raw materials for the reaction. In order to effectively carry out the dehydration, an azeotropic dehydrator may be used. No particular restriction is put on a kind of azeotropic dehydrator, but a hydrocarbon solvent is usually used. Examples of the hydrocarbon solvent include aliphatic hydrocarbons such as hexane, heptane, octane, nonane, decane, undecane, dodecane, ligroin and kerosene, aromatic hydrocarbons such as benzene, toluene, xylene, mesitylene, ethylbenzene, cumene, diphenyl ether and naphthalene, and halogenated hydrocarbons such as 1,2-dichloroethane, 1,1,2-trichloroethane, chlorobenzene, o-dichlorobenzene and p-dichlorobenzene. These can be used singly or in a combination of two or more thereof. The amount of the azeotropic dehydrator to be used depends on the amount of water entrained into the system, but it is usually 2 to 10 times by weight as much as the amount of the water in the system. After the completion of the dehydration, the used azeotropic dehydrator may be distilled off from the system or it may remain in the system and then forwarded to the next reaction.

In the present invention, the reaction by which the alkali metal salt of the phenol is produced from the phenol and the alkali metal compound is carried out under atmospheric pressure or reduced pressure. At this time, a reaction temperature depends on a kind of selected azeotropic dehydrator and a vacuum degree, but water distilled by heating the reaction mixture up to an azeotropic temperature of the azeotropic dehydrator and water under this vacuum degree is removed from the system. At this time, the azeotropic dehydrator distilled off together with water may be returned to the system as it is, or it may freshly be added as much as distilled off.

No particular restriction is put on the reaction of the thus obtained alkali metal salt of the phenol and carbon dioxide, but it is usually carried out in an autoclave at a reaction temperature of 80 to 200° C. under a carbon dioxide gas pressure of 1 to 20 $kg/cm^2$.

The reaction time depends on the reaction temperature and the carbon dioxide gas pressure, but usually, a time of about 1 to 6 hours is enough. Depending on the kind of raw material phenol or produced hydroxybenzoic acid, the reaction system becomes a paste so that stirring is difficult sometimes after the production of the hydroxybenzoic acid. In this case, a lubricant which is inert to the reaction may be previously added and the reaction with carbon dioxide may be then carried out, which does not provide any influence on the reaction yield. No particular restriction is put on the kind of lubricant, but a hydrocarbon solvent is usually used in consideration of a reaction morphology and handling ease. Examples of the hydrocarbon solvent include aliphatic hydrocarbons such as hexane, heptane, octane, nonane, decane, undecane, dodecane, ligroin and kerosene, aromatic hydrocarbons such as benzene, toluene, xylene, mesitylene, ethylbenzene, cumene, diphenyl ether and naphtha lene, and halogenated hydrocarbons such as 1,2-dichloroethane, 1,1,2-trichloroethane, chlorobenzene, o-dichlorobenzene and p-dichlorobenzene.

The thus obtained alkali metal salt of the hydroxybenzoic acid is crystallized by a means such as cold crystallization or reprecipitation by the use of a poor solvent, and then isolated by a conventional solid-liquid separating operation such as filtration or centrifugal separation. Examples of the poor solvent which can be used include hydrocarbon solvents, and typical examples of the hydrocarbon solvents include aliphatic hydrocarbons such as hexane, heptane, octane, nonane, decane, undecane, dodecane, ligroin and kerosene, aromatic hydrocarbons such as benzene, toluene, xylene, mesitylene, ethylbenzene, cumene, diphenyl ether, and naphthalene, and halogenated hydrocarbons such as 1,2-dichloroethane, 1,1,2-trichloroethane, chlorobenzene, o-dichlorobenzene and p-dichlorobenzene, and these can be used singly or in a combination of two or more thereof. The hydrocarbon solvent which can be used as the poor solvent may be the same as or different from the hydrocarbon solvent usable as the above azeotropic dehydrator and lubricant, but it is preferable to use the same solvent in consideration of the recovery of the solvent.

The obtained wet alkali metal salt of the hydroxybenzoic acid is dissolved in water, and the organic layer mainly comprising the used hydrocarbon solvent is separated and removed. The resulting aqueous layer is neutralized with a mineral acid such as hydrochloric acid, sulfuric acid and nitric acid, and the precipitated crystals are isolated by a solid-liquid separating operation such as filtration and centrifugal separation to obtain the substantially impurities-free hydroxybenzoic acid. When the washing of the wet alkali metal salt of the hydroxybenzoic acid is insufficient, the aqueous layer obtained by the separation contains the phenol. In this case, the same hydrocarbon solvent is added and extraction/separation is done so that the phenol may transfer into the organic layer, and the resulting aqueous layer is then neutralized with a mineral acid such as hydrochloric acid, sulfuric acid and nitric acid, and the precipitated crystals are isolated by a solid-liquid separating operation such as filtration and centrifugal separation to obtain the substantially impurities-free hydroxybenzoic acid.

In the present invention, the recovered solution from which the alkali metal salt of the hydroxybenzoic acid has been separated substantially comprises the phenol, the aprotic polar organic solvent and the hydrocarbon solvent used as the azeotropic dehydrator and as the lubricant. Thus, after the hydrocarbon solvent has been recovered by an operation such as distillation, the recovered solution is returned to the raw material system, and the alkali metal compound and the phenol are added as much as their consumed amounts to rebuild the reaction recycle system. In a certain case, the recovered solution contains small amounts of the alkali metal salt of the hydroxybenzoic acid and inorganic salts, but in such a case, the recovered solution is washed with a small amount of water and extracted so that the alkali metal salt of the hydroxybenzoic acid and the inorganic salts may transfer into the aqueous layer. Afterward, the hydrocarbon solvent is recovered by an operation such as distillation, and the recovered solution is returned to the raw material system, and the alkali metal compound and the phenol are added as much as their consumed amounts to rebuild the reaction recycle system. Moreover, the recovered hydrocarbon solvent can be used again as the azeotropic dehydrator and the lubricant.

As described above, according to the present invention, there can be provided an industrially applicable process for preparing a hydroxybenzoic acid from a phenol in accordance with the Kolbe-Schmidt reaction by the use of an aprotic polar organic solvent as a reaction solvent. This process is excellent in a reaction yield and a product take out yield and can substantially completely recycle the used aprotic polar organic solvent.

EXAMPLES

Next, the present invention will be described in more detail with reference to examples, but the scope of the present invention should not be limited to these examples only.

In this connection, 3,5-di-tert-butylsalicylic acid (hereinafter abbreviated to "DBSA") and various hydroxybenzoic acids were analyzed by a high-performance liquid chromatography (HPLC), 1,3-dimethyl-2-imidazolidinone (hereinafter abbreviated to "DMi") and sulfolane were analyzed by a gas chromatography (GC), and a Na content was analyzed by a hydrochloric acid titration.

Example 1

In a 200 ml four-necked flask were placed 74.29 g (0.36 mol) of 2,4-di-tert-butylphenol (hereinafter abbreviated to "DBP"), 6.16 g (0.054 mol) Dmi, of 20 g of toluene and 4.9 g (0.06 mol) of a 49 wt % aqueous NaOH solution, and azeotropic dehydration was then carried out under heating. After a stoichiometric amount of water was distilled, the reaction solution was put in a 300 ml autoclave, and 75 g of toluene was added. Afterward, the solution was heated up to 120° C. and then allowed to absorb a carbon dioxide gas at 6 kg/cm²G. and reaction was carried out for 5 hours under the same pressure. In this case, a conversion was 88.0%/NaOH. The resulting reaction solution was cooled to 70° C. and then allowed to mature for 2 hours. Next, filtration .and washing were done to collect the resulting sodium 3,5-di-tert-butylsalicylate (hereinafter abbreviated to "DBSA-Na"). According to analysis, a DMi content in this wet product was not detected, and it was confirmed that the total amount of DMi was present in the filtrate and the wash liquid. The wet product was dissolved in 36 g of water at 60° C., and the toluene layer was separated and removed. Afterward, toluene dissolved in the aqueous layer was distilled off under heating. The remaining aqueous layer was added dropwise to 44.2 g of 6 wt % sulfuric acid over 2 hours to carry out acidifying-out, and the resulting precipitate was filtered, washed and then dried to obtain DBSA. Its purity was 99.8%, and its yield was 85.0%/NaOH.

Example 2

In a 200 ml four-necked flask were placed 74.29 g (0.36 mol) of DBP, 11.99 g (0.105 mol) of DMi, 27 g of toluene and 4.9 g (0.06 mol) of a 49 wt % aqueous NaOH solution, and azeotropic dehydration was then carried out under heating. After a stoichiometric amount of water was distilled, the reaction solution was put in a 300 ml autoclave, and 75 g of toluene was added. Afterward, the solution was heated up to 120° C. and then allowed to absorb a carbon dioxide gas at 6 kg/cm²G, and reaction was carried out for 5 hours under the same pressure. In this case, a conversion was 92.2%/NaOH. The resulting reaction solution was cooled to 80° C., and 100 g of hexane was added thereto under the same pressure. Next, filtration and washing were done to collect the resulting DBSA-Na. This wet DBSA-Na did not contain any DMi. The wet product was dissolved in 40 g of water at 60° C., and the toluene layer was separated and removed. Afterward, toluene dissolved in the aqueous layer was distilled off under heating. The remaining aqueous layer was added drop-wise to 44.2 g of 6 wt % sulfuric acid over 2 hours to carry out acidifying-out, and the resulting precipitate was filtered, washed and then dried to obtain DBSA. Its purity was 99.8%, and its yield was 84.8%/NaOH.

Example 3

In Example 1, a filtrate and a wash liquid in the step of the take out of DBSA-Na by filtration were mixed with each other, and toluene was distilled off under heating to obtain a solution substantially comprising DBP, DMi and a solubility content of DBSA-Na. Next, 4.41 g of 49 wt % NaOH, 10.52 g of DBP and 20 g of toluene were added to the solution, and the same procedure as in Example 1 was conducted. In consequence, DBSA having a purity of 99.8% was obtained in a yield of 98%/addition DBP.

Example 4

In a four-necked flask were placed 49.53 g (0.240 mol) of DBP, 2.05 g (0.018 mol) of DMi and 40 g of xylene, and the solution was heated until reflux began. Next, azeotropic dehydration was carried put, while 4.41 g (0.054 mol) of a 49 wt % aqueous NaOH solution was added dropwise over 2 hours. Afterward, 20 g of xylene was added dropwise, and the solution was allowed to mature under the reflux for 2 hours. It was confirmed that a stoichiometric amount of water was distilled. The reaction solution was put in a 300 ml autoclave, heated up to 120° C., and then allowed to absorb a carbon dioxide gas at 6 kg/cm²G, followed by maturation at the same temperature for 5 hours. In this case, a conversion was 92.1%/NaOH. The reaction solution was slowly cooled to 70° C., and then crystallized at 70° C. for 2 hours. The reaction solution (a DBSA-Na slurry solution) was filtered at the same temperature, and then washed three times with 20 g of xylene to obtain 35.57 g of wet DBSA-Na. According to analysis, the amounts of wet DBSA and a Na content were 34.0 wt % and 3.12 wt %, respectively, and any DMi was not contained. Furthermore, the recovery yield of DBSA-Na was 90%/NaOH. It was confirmed that DMi was completely recovered in a filtrate and a wash liquid in the steps of the heating, the filtration and the washing. The wet product was dissolved in 54 g of water at 60° C., and an extraction operation was carried out twice with 18 g of xylene to obtain an aqueous layer. Xylene dissolved in this aqueous layer was distilled off under reduced pressure, and the aqueous layer was added dropwise to 49 g of a 6% sulfuric acid solution over 2 hours to carry out acidifying-out, thereby obtaining an aqueous DBSA slurry solution. Next, this aqueous slurry solution was filtered, and then washed three times with 12 g of water to recovery wet DBSA, and this wet DBSA was dried. In consequence, 12.0 g of DBSA was obtained, and its purity was 99.9% or more. A total take out yield in terms of pure DBSA from the raw material was 89.7%/NaOH.

Example 5

From a mixture of a filtrate and a wash liquid in the step of the filtration of DBSA-Na obtained in a recovery yield of 90%/NaOH in Example 4, xylene was distilled off under heating to prepare a solution substantially comprising DBP, DMi and a solubility content of DBSA-Na (2 mol%/NaOH). Next, 10.03 g of DBP and 40 g of xylene were added to the solution, and the solution was heated until reflux began.

While 4.06 g of a 49 wt % aqueous NaOH solution was added dropwise, azeotropic dehydration was carried out, and afterward, the same procedure as in Example 4 was conducted. As a result, DBSA having a purity of 99.8% was obtained in a yield of 98%/addition DBP.

In the mixture of the filtrate and the wash liquid in the step of the filtration of DBSA-Na, 5 mol %/(produced DBSA-Na) of DBSA-Na was dissolved. The mixture was washed at 60° C. with 5 g of water to extract the total of DBSA-Na in the aqueous layer. In the aqueous extraction layer, 1 mol %/(the feed) of DMi was lost. After the extraction, xylene was similarly distilled off from the organic layer, and 9.83 g of DBP, 40 g of xylene and 1 mol % of DMi were added. Next, the solution was heated until reflux began, and azeotropic dehydration was carried out, while 3.98 g of a 49 wt % aqueous NaOH solution was added dropwise. Afterward, in accordance with the same procedure as in Example 4, reaction was carried out. The resulting wet DBSA-Na was dissolved in 54 g of water at 60° C., and the solution was then mixed with the aqueous extraction layer of the above recovered mixture of the filtrate and the wash liquid. The solution was washed with xylene, and then separated to obtain an aqueous layer. Xylene dissolved in the aqueous layer was distilled off under reduced pressure, and the solution was then added dropwise to 49 g of a 6% sulfuric acid solution over 2 hours to carry out acidifying-out, thereby obtaining DBSA. In consequence, purity was 99.8%, and yield was 98.1%/(addition DBP).

Afterward, the similar operation was repeated 6 times, but problems did not occur with regard to reaction yield, recovery yield, product purity and DMi loss percent.

Example 6

In a 200 ml four-necked flask were placed 74.29 g (0.36 mol) of DBP, 11.99 g (0.105 mol) of sulfolane, 20 g of toluene and 4.9 g (0.06 mol) of a 49 wt % aqueous NaOH solution, and azeotropic dehydration was then carried out under heating. After a stoichiometric amount of water was distilled, the reaction solution was put in a 300 ml autoclave, and 75 g of toluene was then added. Afterward, the solution was heated up to 120° C. and then allowed to absorb a carbon dioxide gas at 6 kg/cm$^2$G, and reaction was carried out for 5 hours under the same pressure. In this case, a conversion was 88.0%/NaOH. The resulting reaction solution was cooled to 45° C. and then allowed to mature for 2 hours. Next, the precipitate of the resulting DBSA-Na was filtered and washed to collect DBSA-Na. It was confirmed that sulfolane was not contained in the wet product and the total amount of sulfolane was contained in the filtrate and the wash liquid. Wet DBSA-Na was dissolved in 36 g of water at 60° C., and the organic layer was separated and removed. Afterward, toluene dissolved in the aqueous layer was distilled off under heating. The remaining aqueous layer was added drop wise to 44.2 g of 6 wt % sulfuric acid over 2 hours to crystallize, and the resulting precipitate was filtered, washed and then dried to obtain DBSA. Its purity was 99.8%, and its yield was 70.0%/NaOH. On the other hand, the filtrate and the wash liquid in the step of the filtration of DBSA-Na were mixed with each other, and the mixture was then-distilled under heating to recover toluene, thereby obtaining a solution substantially comprising DBP, sulfolane and a solubility content of DBSA-Na. To this solution, 3.43 g of 49 wt % NaOH, 8.67 g of DBP and 20 g of recovered toluene were added, and the formation of DBP-Na and the Kolbe-Schmidt reaction were carried out again. Afterward, the solution was taken out by the same procedure as described above to obtain DBSA having a purity of 99.8% in a yield of 98%/addition DBP.

Example 7

In a 200 ml four-necked flask were placed 43.97 g (0.36 mol) of 2,4-xylenol, 6.8 g (0.06 mol) of DMi, 20 g of toluene, 2.50 g (0.06 mol) of a 96 wt % NaOH flake and 1.08 g of water, and azeotropic dehydration was then carried out. After a stoichiometric amount of water was distilled, the reaction solution was put in a 300 ml autoclave and then allowed to absorb a carbon dioxide gas, and reaction was carried out at 120° C. under 6 kg/cm$^2$G for 6 hours. In this case, a conversion was 90.3%/the raw material 2,4-xylenol. The resulting reaction solution was poured into 100 g of toluene, and then allowed to mature at 5° C. Next, the resulting precipitate was filtered and washed to obtain wet 3,5-dimethylsalicylic acid-Na. This wet product was dissolved in 75 g of water, and the toluene layer was separated and removed. Afterward, the aqueous layer was added dropwise to 210 g of 5 wt % sulfuric acid over 2 hours to crystallize, and the precipitated crystals were filtered, washed and then dried to obtain 3,5-dimethylsalicylic acid. Its purity was 99.0%, and its yield was 72.0%/the raw material 2,4-xylenol.

Example 8

In a 200 ml four-necked flask were placed 41.26 g (0.20 mol) of DBP, 15 g of toluene, 68.4 g (0.60 mol) 7 of DMi and/6.33 g (0.20 mol) of a 49 wt % aqueous NaOH solution, and azeotropic dehydration was then carried out. After a substantially stoichiometric amount of water was distilled, toluene was distilled off under reduced pressure, and the reaction solution was put in a 300 ml autoclave. Afterward, the solution was heated up to 120° C. and then allowed to absorb a carbon dioxide gas at 6 kg/cm$^2$G, and reaction was carried out for 5 hours under the same pressure. In this case, a conversion was 89%/raw material DBP. After the pressure was released, 747.6 g (1.20 mol) of DBP was added to the resulting reaction solution, and maturation was then done at 120° C. for 2 hours. Next, 150 g of toluene was added to the solution, and the mixture was cooled on ice and continuously stirred for 1 hour. The resulting DBSA-Na precipitate was filtered, and then washed three times with toluene to obtain wet DBSA-Na. The recovery yield was 76%/NaOH. As a result of analysis, any DMi was not contained in the wet product, and the total amount of DMi was contained in the filtrate and the wash liquid. For the obtained wet product, the same procedure as in Example 1 was conducted to obtain DBSA having a purity of 99.7% in a yield of 75.7%/NaOH.

Example 9

In a 200 ml four-necked flask were placed 49.53 g (0.240 mol) of 2,6-di-tert-butylphenol (hereinafter abbreviated to "2,6-DBP"), 2.05 g (0.018 mol) of DMi and 40 g of xylene, and the solution was heated until reflux begun. Afterward, azeotropic dehydration was carried out, while 4.41 g (0.054 mol) of a 49 wt % aqueous NaOH solution was added dropwise over 5 hours. Next, 20 g of xylene was added dropwise, and the solution was allowed to mature under the reflux for 2 hours. It was confirmed that a stoichiometric amount of water was distilled. The reaction solution was put in a 300 ml autoclave, heated up to 160° C., and then allowed to absorb a carbon dioxide gas at 6 kg/cm$^2$G, followed by maturation at the same temperature for 5 hours. In this case, a conversion was 90.0%/NaOH. The reaction solution was slowly cooled to 70° C., and then crystallized at 70° C. for 2 hours. The reaction solution was filtered at the same temperature, and then washed three times with 20 g of xylene to obtain wet sodium 3,5-ditert-butyl-4- hydroxybenzoate. According to analysis, the recovery yield of sodium 3,5-di-tert-butyl-4-hydroxybenzoate was 88.4%/NaOH, and any DMi was not detected. It was confirmed that DMi was completely recovered in a filtrate and a wash liquid in the steps of the heating, the filtration and the washing. The wet product was dissolved in 54 g of water at 60° C., and an extraction operation was carried out twice with 18 g of xylene to obtain an aqueous layer. Xylene dissolved in this aqueous layer was distilled off under reduced pressure, and the aqueous layer was added dropwise to 49 g of a 6% sulfuric acid solution over 2 hours to crystallize. The resulting precipitate was filtered, and then washed three times with 12 g of water. Next, wet 3,5-di-tert-butyl-4-hydroxybenzoic acid was taken out, and then dried to obtain 12.0 g of 3,5-di-tert-butyl-4-hydroxybenzoic acid, and a purity was 99.9% or more and a total recovery yield in terms of pure product from the raw material was 88.0%/NaOH.

Example 10

In a 200 ml four-necked flask were placed 49.53 g (0.240 mol) of 4-tert-octylphenol, 2.05 g (0.018 mol) of DMi and 40 g of xylene, and the solution was heated until reflux begun. Afterward, azeotropic dehydration was carried out, while 4.41 g (0:054 mol) of a 49 wt % aqueous NaOH solution was added dropwise over 5 hours. Next, 20 g of xylene was added dropwise, and the solution was allowed to mature under the reflux for 2 hours. It was confirmed that a stoichiometric amount of water was distilled. The reaction solution was put in a 300 ml autoclave, heated up to 130° C., and then allowed to absorb a carbon dioxide gas at 6 kg/cm$^2$G, followed by maturation at the same temperature for 5 hours. In this case, a conversion was 86.7%/NaOH. The reaction solution was slowly cooled to 70° C., and then crystallized at 70° C. for 2 hours. The reaction solution was filtered at the same temperature, and then washed three times with 20 g of xylene to obtain wet sodium 5-tert-octylsalicylate. According to analysis, the recovery yield of sodium 5-tert-octylsalicylate was 85.3%/NaOH, and any DMi was not detected. It was confirmed that DMi was completely recovered in a filtrate and a wash liquid in the steps of the heating, the filtration and the washing. The wet product was dissolved in 54 g of water at 60° C., and an extraction operation was carried out twice with 18 g of xylene to obtain an aqueous layer. Xylene dissolved in this aqueous layer was distilled off under reduced pressure, and the aqueous layer was added dropwise to 49 g of a 6% sulfuric acid solution over 2 hours to crystallize. The resulting precipitate was filtered, and then washed 3 times with 12 g of water. Next, wet 5-tert-octylsalicylic acid was taken out, and then dried to obtain 11.52 g of 5 tert-octylsalicylic acid. In this case, a purity was 99.9% or more and a total recovery yield in terms of pure product from the raw material was 85.2%/NaOH.

Example 11

In a 200 ml four-necked flask were placed 29.79 g (0.240 mol) of 4-methoxyphenol, 2.05 g (0.018 mol) of DMi and 40 g of xylene, and the solution was heated 4 until reflux began. Afterward, azeotropic dehydration was carried out, while 4.41 g (0.054 mol) of a 49 wt % aqueous NaOH solution was added dropwise over 5 hours. Next, 20 g of xylene was added dropwise, and the solution was allowed to mature under the reflux for 2 hours. It was confirmed that a stoichiometric amount of water was distilled. The reaction solution was put in a 300 ml autoclave, heated up to 160° C., and then allowed to absorb a carbon dioxide gas at 6 kg/cm$^2$G, followed by maturation at the same temperature for 7 hours. In this case, a conversion was 74.9%/NaOH. The reaction solution was slowly cooled to 70° C., and then crystallized at 70° C. for 2 hours. The reaction solution was filtered at the same temperature, and then washed three times with 20 g of xylene to obtain wet sodium 5-methoxysalicylate. According to analysis, the recovery yield of sodium 5-methoxysalicylate was 72.8%/NaOH, and any DMi was not detected. It was confirmed that DMi was completely recovered in a filtrate and a wash liquid in the steps of the heating, the filtration and the washing. The wet product was dissolved in 54 g of water at 60° C., and an extraction operation was carried out twice with 18 g of xylene to obtain an aqueous layer. Xylene dissolved in this aqueous layer was distilled off under reduced pressure, and the aqueous layer was added dropwise to 49 g of a 6% sulfuric acid solution over 2 hours to crystallize. The resulting precipitate was filtered, and then washed three times with 12 g of water. Next, wet 5-methoxysalicylic acid was taken out, and then dried to obtain 6.60 g of 5-methoxysalicylic acid. In this case, a purity was 99.9% or more and a total recovery yield in terms of pure product from the raw material was 72.7%/NaOH.

Comparative Example 1

In a 200 ml four-necked flask were placed 20.63 g (0.1 mol) of DBP, 100 g of toluene, 4.18 g (0.1 mol) of flaky NaOH (purity=96%) and 1.8 g of water, and azeotropic dehydration was then carried out. In the middle of the dehydration, the reaction mass became pasty, so that stirring could not be done. Therefore, 50 g of toluene was added thereto to continue the reaction, but the dehydration was insufficient. In consequence, 70% of a stoichiometric amount of water was merely distilled. This reaction mass was put in an autoclave, and the reaction was carried out at 120° C. under a carbon dioxide gas pressure of 6 kg/cm$^2$G for 5 hours. The conversion was as low as 11.5%/NaOH.

Comparative Example 2

In a 200 ml flask were placed 20.63 g (0.1 mol) of DBP, 100 g of toluene, 3 g (0.026 mol) of DMi and 8.16 g (0.1 mol) of a 49% aqueous NaOH solution, and azeotropic dehydration was then carried out. In the middle of the dehydration, the reaction mass became pasty and so stirring was impossible, so that the azeotropic dehydration was interrupted. This paste was put in an autoclave, and the reaction was carried out at 120° C. under a carbon dioxide gas pressure of 6 kg/cm$^2$G for 5 hours. The conversion was as low as 17.8%/NaOH. After water was added to the reaction solution, the solution was separated, and the resulting aqueous layer was added dropwise to 200 g of a 3% sulfuric acid solution to crystallize. A conversion of the resulting DBSA was 17.7%/NaOH. In addition, the total amount of DMi was present in a filtrate and a wash liquid after the crystallization by acidification.

Comparative Example 3

In a 200 ml four-necked flask were placed.41.26 g (0.2 mol) of DBP, 15 g of toluene, 68.5 g (0.60 mol) of DMi and 16.33 g (0.2 mol) of a 49% aqueous NaOH solution, and azeotropic dehydration was then carried out. After a substantially stoichiometric amount of water was distilled, toluene was distilled off under reduced pressure, and the reaction solution was put in a 300 ml autoclave. Afterward, the solution was heated up to 120° C. and then allowed to absorb a carbon dioxide gas at 6 kg/cm$^2$G, and reaction was carried out for 5 hours under the same pressure. In this case, a conversion was 89%/NaOH. Next, 150 g of toluene was added to the reaction solution, and the mixture was cooled on ice, continuously stirred for 1 hour, filtered, and then washed three times with toluene to obtain 126.2 g of a wet product. As a result of the analysis of the wet product, DBSA was 25.9 wt %, DMi was 11.8 wt %, Na content was 2.4 wt %, recovery yield was 65.3%/DBP, and loss of DMi in the wet product was 21.7%/fed DMI. Next, the wet product was added to 150 g of toluene, and sludging was done under ice cooling with continuous stirring for 0.5 hour. Afterward, the sludge was filtered, and then washed five times with toluene to obtain 96.6 g of the wet product. According to the same analysis as described above, DBSA was 29.3 wt %, DMi was 13.4 wt %, and Na content was 2.7 wt %, and loss of DMi in the wet product was 18.9%/fed DMI. After the wet product was dissolved in 200 g of water and the resulting organic layer was separated, 30 g of toluene was further added to the aqueous layer, and the mixture was then extracted and separated to obtain the aqueous layer. After a dissolved toluene was distilled off under reduced pressure, the aqueous layer was slowly added dropwise to 400 g of a 3% aqueous sulfuric acid solution at room temperature to crystallize, followed by stirring for 0.5 hour. Afterward, the crystallized by acidification solution was filtered and then washed with pure water, and the resulting wet DBSA was then dried to obtain 28.1 g of DBSA in a recovery yield of 56.1%/NaOH. On the other hand, DMi in the filtrate was analyzed, and it revealed that a loss of DMi in a filtrate and a wash liquid was 18.9%/fed DMi. The purity of the obtained DBSA was 99.9% or more, and it was confirmed that no DMi was contained in DBSA.

Comparative Example 4

In Comparative Example 3, toluene was distilled off from a recovered filtrate and wash liquid after the crystallization and separation of DBSA-Na, thereby obtaining an aqueous layer substantially comprising unreacted DBP, DMi and a solubility content of DBSA-Na. To this aqueous layer, there were added 14.53 g of 49% NaOH, 36.72 g of DBP and 12.9 g of DMi, and afterward, the same procedure as in Comparative Example 3 was conducted again. As a result, a reaction yield was as low as 70%/addition NaOH, and even when toluene was added and the solution was cooled on ice, DBSA-Na could not be crystallized and it remained in the state of a uniform solution.

Comparative Example 5

In a 200 ml four-necked flask were placed 74.28 g (0.36 mol) of DBP, 20 g of toluene and 4.9 g (0.06 mol) of a 49% aqueous NaOH solution, and azeotropic dehydration was then carried out under heating. After a substantially stoichiometric amount of water was distilled, the reaction solution was put in a 300 ml autoclave, and 75 g of toluene was added. Afterward, the solution was heated up to 120° C., and then allowed to absorb a carbon dioxide gas at 6 kg/cm²G, and reaction was carried out for 5 hours under the same pressure. The conversion was very low, 12.5%/NaOH.

Comparative Example 6

In a 500 ml flask were placed 41.2 g (0.2 mol) of DBP, 8.4 g (0.21 mol) of sodium hydroxide flake, 70 cc of water, 100 cc of toluene and 120 cc (144 g) of sulfolane. After the system was allowed to stand at 70 to 80° C. for about 1 hour, the solution was heated up to a temperature at which reflux began, and water was removed by toluene-water azeotropic distillation. After about 1.5 hours, the distillation of water ended at a time when the temperature in the reaction system reached 125° C., and a substantially stoichiometric amount of water was recovered. Afterward, this system was further heated up to 165° C. to recover 85 cc of toluene, so that the dehydrated sulfolane solution of DBP-Na was obtained. The solution was put in a pressure-resistant autoclave, and reaction was carried out at 120 to 130° C. under a carbon dioxide pressure of 8 to 9 kg/cm²G for about 6 hours until the absorption of the carbon dioxide gas was not observed any more. The resulting reaction product was taken out from the autoclave, and 128.3 g of sulfolane was then recovered by simple distillation under reduced pressure (recovery ratio= about 89%). Next, 150 cc of water was thrown into the recovered residue, and the system was then heated up to about 90° C. to dissolve the contents. Afterward, 1000 cc of diluted hydrochloric acid was added to adjust a pH to 2 or less, and precipitated pure white DBSA was then collected by filtration. This precipitate was washed with water, and then dried to obtain 42 g of DBSA (isolation yield=84%/ NaOH) having a purity of 99% (HPLC). A mixture of a filtrate and a wash liquid after crystallization by acidification was analyzed, and it was confirmed that a content of sulfolane was about 11%/(used sulfolane).

Comparative Example 7

By the same procedure as in Comparative Example 6, 41.2 g of DBP was carboxylated to obtain a sulfolane solution containing DBSA-Na. To this solution, 280 cc of toluene was added, whereby DBSA-Na was precipitated. The resulting slurry solution was filtered, and then washed three times with 150 cc of toluene to obtain wet DBSA-Na. According to analysis, it was confirmed that 15.0 g of sulfolane was present in the wet product (loss=10.4%/used sulfolane). This wet product was dissolved in 150 cc of water, and 1000 cc of diluted hydrochloric acid was added thereto, thereby adjusting a pH to 2 or less, and consequently a DBSA slurry solution was obtained. This slurry solution was filtered to obtain DBSA. On the other hand, a filtrate obtained at the filtration of DBSA was analyzed, and it was confirmed that sulfolane was contained in the aqueous solution. Its recovery operation was not conducted.

Comparative Example 8

In a 200 ml flask were placed 20.63 g (0.1 mol) of DBP, 100 g of toluene, 3 g of sulfolane and 11.68 g (0.1 mol) of a 49 wt % aqueous KOH solution, and azeotropic dehydration was then carried out. In the middle of the reaction, a reaction mass became pasty and so stirring was impossible, so that the dehydration reaction was interrupted. This paste was put in an autoclave, and the reaction was carried out at 120° C. under a carbon dioxide gas pressure of 6 kg/cm²G for 5 hours. The conversion was as low as 15.2%/NaOH.

According to a process of the present invention, there can be provided an industrially suitable process for preparing a hydroxybenzoic acid from a phenol in accordance with the Kolbe-Schmidt reaction by the use of an aprotic polar organic solvent as a reaction solvent, and this process is excellent in a reaction yield and a product recovery yield and can substantially completely recycle the used aprotic polar organic solvent.

What is claimed is:

1. A process for preparing a hydroxybenzoic acid which comprises the steps of (1) reacting a phenol with an alkali metal compound by using an aprotic polar organic solvent as a reaction solvent to form an alkali metal salt of the phenol, (2) reacting the alkali metal salt with carbon dioxide to obtain an alkali metal salt of hydroxybenzoic acid, and (3) separating the alkali metal salt of hydroxybenzoic acid from the reaction solution wherein the molar ratio is controlled such that in the reaction solution in step (3) the molar ratio of phenol:alkali metal salt of hydroxybenzoic acid is 1–9:1, the molar ratio of phenol: aprotic polar organic solvent is larger than 1:1, and the remaining solution after separating the alkali metal salt of hydroxybenzoic acid is returned to step (1) after supplying fresh alkali metal compound and phenol to the solution in amounts corresponding to the converted hydroxybenzoic acid.

2. The process according to claim 1, wherein the control is carried out at step (1).

3. The process according to claim 1, wherein the molar ratio of the phenol to the alkali metal compound is at least 1 in step (1) and the molar ratio of the phenol to the alkali metal salt of the hydroxybenzoic acid and the aprotic polar organic solvent in the solution in step (3) is controlled by adding phenol to the reaction solvent after step (2).

4. The process according to claim 1, wherein, in step (1), the molar ratio of the phenol to the alkali metal compound is 2–10, and the molar ratio of the phenol to the aprotic polar organic solvent is 2–30, and wherein the molar ratio of the aprotic polar organic solvent to the alkali metal compound is in the range of 0.3 to 3.

5. The process according to claim 1 wherein the aprotic polar organic solvent is 1,3-dimethyl-2-imidazolidinone.

6. The process according to claim 1 wherein the aprotic polar organic solvent is sulfolane.

7. The process according to claim 1 wherein the phenol is a 2,4-dialkylphenol and the hydroxybenzoic acid is a 3,5-diallylsalicylic acid.

* * * * *

UNITED STATES PATENT AND TRADEMARK OFFICE
CERTIFICATE OF CORRECTION

PATENT NO. : 6,392,090 B1
DATED : May 21, 2002
INVENTOR(S) : Masayuki Furuya et al.

It is certified that error appears in the above-identified patent and that said Letters Patent is hereby corrected as shown below:

<u>Title page,</u>
Item [56], References Cited, add the following U.S. references:

| | | | |
|---|---|---|---|
| -- 4,814,495 | 5/21/89 | Sakai et al. | 562/424 |
| 4,034,006 | 7/5/77 | Lind et al. | 562/424 |
| 4,376,867 | 3/15/83 | Jansen et al. | 562/424 |
| 4,966,992 | 10/30/90 | Ueno et al. | 562/424 |
| 4,072,707 | 2/7/78 | Grosso | 562/424 |
| 4,950,781 | 8/21/90 | Nakanishi et al | 562/424 |
| 4,730,083 | 3/8/88 | Pastor et al | 562/423 -- |

Signed and Sealed this

Twenty-fifth Day of February, 2003

JAMES E. ROGAN
*Director of the United States Patent and Trademark Office*